United States Patent [19]
Cohen

[11] Patent Number: 5,998,308
[45] Date of Patent: Dec. 7, 1999

[54] NONWOVEN BARRIER AND METHOD OF MAKING THE SAME

[75] Inventor: Bernard Cohen, Berkeley Lake, Ga.

[73] Assignee: Kimberly-Clark Worldwide, Inc., Neenah, Wis.

[21] Appl. No.: 08/651,401

[22] Filed: May 22, 1996

Related U.S. Application Data

[63] Continuation of application No. 08/198,928, Feb. 22, 1994, abandoned.

[51] Int. Cl.$^6$ .................................................... D04H 1/58
[52] U.S. Cl. ...................... 442/110; 442/114; 442/392; 427/394; 264/22
[58] Field of Search ........................ 428/289; 427/394; 264/22; 442/110, 114, 392

[56] References Cited

U.S. PATENT DOCUMENTS

| | | |
|---|---|---|
| Re. 30,782 | 10/1981 | van Turnhout .............................. 264/22 |
| Re. 31,285 | 6/1983 | van Turnhout et al. ................... 55/155 |
| Re. 32,171 | 6/1986 | van Turnhout .............................. 55/155 |
| 668,791 | 2/1901 | Blake et al. . |
| 813,063 | 2/1906 | Sutton et al. . |
| 859,998 | 7/1907 | Wentworth . |
| 924,032 | 6/1909 | Blake et al. . |
| 1,222,305 | 4/1917 | Kraus . |
| 1,297,159 | 3/1919 | Hedberg . |
| 1,355,477 | 10/1920 | Howell . |
| 2,106,865 | 2/1938 | Bantz et al. .............................. 209/127 |
| 2,217,444 | 10/1940 | Hill ............................................. 91/18 |
| 2,328,577 | 9/1943 | Oglesby .................................... 117/17 |
| 2,378,067 | 3/1945 | Cook, Jr. ................................. 209/127 |
| 2,398,792 | 4/1946 | Johnson ................................... 209/127 |
| 2,748,018 | 5/1956 | Miller ........................................ 117/17 |
| 2,998,051 | 8/1961 | Sittel ........................................ 154/1.7 |
| 3,012,668 | 12/1961 | Fraas ....................................... 209/127 |
| 3,125,547 | 3/1964 | Blatz ....................................... 260/45.5 |
| 3,281,347 | 10/1966 | Winder ................................... 204/168 |
| 3,323,933 | 6/1967 | Barford et al. ........................... 117/17 |
| 3,338,992 | 8/1967 | Kinney ..................................... 264/24 |
| 3,341,007 | 9/1967 | Mayer et al. ............................. 209/2 |
| 3,341,394 | 9/1967 | Kinney ..................................... 161/72 |
| 3,380,584 | 4/1968 | Fulwyler ................................... 209/3 |
| 3,402,814 | 9/1968 | Morel et al. ............................. 209/127 |
| 3,502,763 | 3/1970 | Hartmann ............................... 264/210 |
| 3,542,615 | 11/1970 | Dobo et al. ............................. 156/181 |
| 3,581,886 | 6/1971 | Singewald et al. ....................... 209/9 |
| 3,692,618 | 9/1972 | Dorschner et al. ...................... 161/72 |
| 3,802,817 | 4/1974 | Matsuki et al. ........................... 425/66 |
| 3,821,021 | 6/1974 | McMillin ............................... 117/135.5 |
| 3,849,241 | 11/1974 | Butin et al. .............................. 161/169 |
| 3,855,046 | 12/1974 | Hansen et al. .......................... 161/150 |
| 3,859,330 | 1/1975 | Proskow .............................. 260/47 UA |
| 3,896,802 | 7/1975 | Williams ................................. 128/149 |
| 3,907,604 | 9/1975 | Prentice .................................. 136/146 |
| 3,909,009 | 9/1975 | Cvetko et al. ............................ 274/37 |
| 3,962,386 | 6/1976 | Driscoll ................................... 264/22 |
| 3,979,529 | 9/1976 | Rebentisch et al. ...................... 427/25 |
| 3,998,916 | 12/1976 | van Turnhout .......................... 264/22 |

(List continued on next page.)

FOREIGN PATENT DOCUMENTS

| | | |
|---|---|---|
| 1188452 | 6/1985 | Canada .......................... A41D 13/00 |
| 0 125 851 | 11/1984 | European Pat. Off. .......... D21C 9/00 |
| 0 156 160 | 10/1985 | European Pat. Off. ........ A61L 15/00 |
| 0334829 | 9/1989 | European Pat. Off. . |
| 0337662 | 10/1989 | European Pat. Off. . |
| 0 375 234 | 6/1990 | European Pat. Off. . |
| 0 391 725 | 10/1990 | European Pat. Off. . |
| 0444671 A | 9/1991 | European Pat. Off. . |
| 0462574 A1 | 12/1991 | European Pat. Off. . |
| 0 478 011 | 4/1992 | European Pat. Off. ........ A61F 13/15 |
| 0 497 072 | 8/1992 | European Pat. Off. ........ A61F 13/15 |
| 0 520 798 | 12/1992 | European Pat. Off. ......... D04H 1/42 |
| 0 550 029 | 7/1993 | European Pat. Off. . |
| 0 575 629 | 12/1993 | European Pat. Off. . |
| 0 576 738 | 1/1994 | European Pat. Off. ........ A61F 13/15 |
| 0594123 | 4/1995 | European Pat. Off. . |
| 0 754 796 | 1/1997 | European Pat. Off. . |
| 44 47 152 | 7/1995 | Germany ...................... A61L 15/60 |
| 1-246413 | 10/1989 | Japan . |
| 5-064713 | 3/1993 | Japan . |
| 2 026 379 | 2/1980 | United Kingdom ............ D06M 9/00 |
| 2 242 142 | 9/1991 | United Kingdom ............. B03C 3/28 |
| 81/03265 | 11/1981 | WIPO . |
| 90/11784 | 10/1990 | WIPO . |
| 91/08254 | 6/1991 | WIPO . |
| 92/16681 | 10/1992 | WIPO ............................. D04H 1/42 |
| 93/06168 | 4/1993 | WIPO . |
| 93/09156 | 5/1993 | WIPO ............................. C08G 8/18 |
| 94/01068 | 1/1994 | WIPO . |
| WO 94/00166 | 1/1994 | WIPO . |
| 95/05232 | 2/1995 | WIPO . |
| 95/05501 | 2/1995 | WIPO . |
| 95/22646 | 8/1995 | WIPO . |
| 96/00093 | 1/1996 | WIPO . |
| 96/28597 | 9/1996 | WIPO . |
| 97/04155 | 2/1997 | WIPO . |

OTHER PUBLICATIONS

Database WPI, Section Ch, Week 8428, Derwent Publications Ltd., London, GB, Class A87, AN 84–173431, XP002008760, & JP,A,59 094 621 (Unitika KK), May 31, 1984, see abstract.

Patent Abstracts of Japan, vol. 10, No. 71 (C–334), Mar. 20, 1986 & JP,A,60 209220 (Kouken K.K.), Oct. 21, 1985, see abstract.

Patent Abstracts of Japan, vol. 6, No. 191 (C–127), Sep. 30, 1982 & JP,A,57 105217 (Nitta K.K.), Jun. 30, 1982, see abstract & Chemical Abstracts, vol. 97, No. 26, Dec. 27, 1982, Columbus, Ohio, US; abstract No. 218901, "Fibrous Filtering Material", see abstract.

(List continued on next page.)

*Primary Examiner*—Christopher Raimund
*Attorney, Agent, or Firm*—Jones & Askew; Nancy M. Klembus

[57] ABSTRACT

A steam sterilizable nonwoven material which is subjected to charging, and more particularly electrostatic charging is provided. The nonwoven materials may include laminate nonwovens wherein one or more layers are subjected to charging. The nonwoven material(s) are treated with an antistatic material before charging.

21 Claims, No Drawings

U.S. PATENT DOCUMENTS

| | | | |
|---|---|---|---|
| 4,011,067 | 3/1977 | Carey, Jr. | 55/354 |
| 4,013,816 | 3/1977 | Sabee et al. | 428/288 |
| 4,035,164 | 7/1977 | Taylor . | |
| 4,041,203 | 8/1977 | Brock et al. | 428/157 |
| 4,058,724 | 11/1977 | McKinney et al. . | |
| 4,070,218 | 1/1978 | Weber | 156/167 |
| 4,091,140 | 5/1978 | Harrnon . | |
| 4,096,289 | 6/1978 | Nischwitz et al. | 427/32 |
| 4,103,062 | 7/1978 | Aberson et al. | 428/283 |
| 4,140,607 | 2/1979 | Kreiseimeier et al. | 204/168 |
| 4,170,304 | 10/1979 | Huke . | |
| 4,178,157 | 12/1979 | van Turnhout et al. | 55/155 |
| 4,185,972 | 1/1980 | Nitta et al. . | |
| 4,196,245 | 4/1980 | Kitson et al. | 428/198 |
| 4,208,366 | 6/1980 | Kinney . | |
| 4,209,563 | 6/1980 | Sisson | 428/288 |
| 4,215,682 | 8/1980 | Kubik et al. | 128/205.29 |
| 4,223,677 | 9/1980 | Anderson | 128/287 |
| 4,273,635 | 6/1981 | Beraud et al. | 204/165 |
| 4,298,440 | 11/1981 | Hood | 204/165 |
| 4,305,797 | 12/1981 | Knoll et al. | 204/180 R |
| 4,307,143 | 12/1981 | Meitner | 252/91 |
| 4,308,223 | 12/1981 | Stern | 264/22 |
| 4,310,478 | 1/1982 | Balslev et al. . | |
| 4,323,374 | 4/1982 | Shinagawa et al. . | |
| 4,324,198 | 4/1982 | Muz | 118/630 |
| 4,340,563 | 7/1982 | Appel et al. | 264/518 |
| 4,342,812 | 8/1982 | Selwood | 428/286 |
| 4,353,799 | 10/1982 | Leonard | 210/321.3 |
| 4,357,234 | 11/1982 | Inculet et al. | 209/127 B |
| 4,363,682 | 12/1982 | Thiebault . | |
| 4,363,723 | 12/1982 | Knoll et al. | 209/128 |
| 4,373,224 | 2/1983 | Bandai et al. . | |
| 4,374,727 | 2/1983 | Takahashi et al. | 209/127 B |
| 4,374,888 | 2/1983 | Bornslaeger | 428/198 |
| 4,375,718 | 3/1983 | Wadsworth et al. | 29/592 |
| 4,392,876 | 7/1983 | Schmidt . | |
| 4,394,235 | 7/1983 | Brandt et al. . | |
| 4,411,795 | 10/1983 | Olson | 210/679 |
| 4,430,277 | 2/1984 | Lin . | |
| 4,443,513 | 4/1984 | Meitner et al. | 422/195 |
| 4,443,515 | 4/1984 | Atlas | 428/224 |
| 4,451,589 | 5/1984 | Morman et al. | 523/124 |
| 4,455,195 | 6/1984 | Kinsley | 162/13 |
| 4,455,237 | 6/1984 | Kinsley | 210/767 |
| 4,456,648 | 6/1984 | Adamse et al. | 428/283 |
| 4,492,633 | 1/1985 | Sandulyak et al. . | |
| 4,507,539 | 3/1985 | Sando et al. | 219/121 PY |
| 4,513,049 | 4/1985 | Yamasaki et al. . | |
| 4,514,289 | 4/1985 | Inculet | 209/127.3 |
| 4,517,143 | 5/1985 | Kisler . | |
| 4,534,918 | 8/1985 | Forrest, Jr. . | |
| 4,547,420 | 10/1985 | Krueger et al. | 428/229 |
| 4,551,378 | 11/1985 | Carey, Jr. | 428/198 |
| 4,554,207 | 11/1985 | Lee | 428/288 |
| 4,555,811 | 12/1985 | Shimalla | 2/51 |
| 4,588,537 | 5/1986 | Klaase et al. | 264/22 |
| 4,592,815 | 6/1986 | Nakao | 204/165 |
| 4,594,626 | 6/1986 | Frangesh . | |
| 4,618,524 | 10/1986 | Groitzsch et al. | 428/198 |
| 4,620,785 | 11/1986 | Watt et al. | 428/219 |
| 4,622,259 | 11/1986 | McAmish et al. | 428/171 |
| 4,623,438 | 11/1986 | Felton et al. | 204/168 |
| 4,626,263 | 12/1986 | Inoue et al. . | |
| 4,652,282 | 3/1987 | Ohmori et al. | 55/155 |
| 4,652,322 | 3/1987 | Lim | 156/181 |
| 4,657,639 | 4/1987 | Mahadevan et al. . | |
| 4,657,804 | 4/1987 | Mays et al. | 428/212 |
| 4,663,220 | 5/1987 | Wisneski | 428/221 |
| 4,670,913 | 6/1987 | Morell et al. | 2/227 |
| 4,671,943 | 6/1987 | Wahlquist . | |
| 4,677,017 | 6/1987 | DeAntonis et al. | 428/214 |
| 4,689,241 | 8/1987 | Richart et al. | 427/28 |
| 4,699,823 | 10/1987 | Kellenberger et al. | 428/219 |
| 4,705,151 | 11/1987 | Eldridge . | |
| 4,707,398 | 11/1987 | Boggs | 428/224 |
| 4,714,647 | 12/1987 | Shipp, Jr. et al. | 428/212 |
| 4,720,415 | 1/1988 | Vander Wielen et al. | 428/152 |
| 4,729,371 | 3/1988 | Krueger et al. | 128/206.19 |
| 4,738,772 | 4/1988 | Giesfeldt | 209/2 |
| 4,739,882 | 4/1988 | Parikh et al. . | |
| 4,749,348 | 6/1988 | Klaase et al. | 425/174.8 |
| 4,761,326 | 8/1988 | Barnes et al. | 428/219 |
| 4,789,504 | 12/1988 | Ohmori et al. . | |
| 4,795,668 | 1/1989 | Krueger et al. | 428/174 |
| 4,797,201 | 1/1989 | Kuppers et al. | 209/127.4 |
| 4,797,318 | 1/1989 | Brooker et al. . | |
| 4,818,464 | 4/1989 | Lau | 264/510 |
| 4,831,664 | 5/1989 | Suda . | |
| 4,847,914 | 7/1989 | Suda . | |
| 4,859,266 | 8/1989 | Akasakiu | 156/273.1 |
| 4,863,785 | 9/1989 | Berman et al. | 428/218 |
| 4,863,983 | 9/1989 | Johnson et al. | 524/140 |
| 4,874,399 | 10/1989 | Reed et al. | 55/2 |
| 4,874,659 | 10/1989 | Ando et al. | 428/221 |
| 4,883,052 | 11/1989 | Weiss et al. . | |
| 4,886,527 | 12/1989 | Fottinger et al. | 55/156 |
| 4,894,131 | 1/1990 | Jacobs et al. | 204/165 |
| 4,901,370 | 2/1990 | Suda . | |
| 4,904,174 | 2/1990 | Moosmayer et al. . | |
| 4,917,942 | 4/1990 | Winters | 428/286 |
| 4,920,168 | 4/1990 | Nohr et al. | 524/188 |
| 4,944,854 | 7/1990 | Felton et al. | 204/168 |
| 4,948,515 | 8/1990 | Okumura et al. | 210/748 |
| 4,948,639 | 8/1990 | Brooker et al. | 428/35.2 |
| 4,960,820 | 10/1990 | Hwo | 524/528 |
| 4,965,122 | 10/1990 | Morman | 428/225 |
| 4,983,677 | 1/1991 | Johnson et al. | 525/127 |
| 5,012,094 | 4/1991 | Hamade . | |
| 5,021,501 | 6/1991 | Ohmori et al. | 524/544 |
| 5,035,941 | 7/1991 | Blackburn | 428/286 |
| 5,051,159 | 9/1991 | Togashi et al. | 204/165 |
| 5,055,151 | 10/1991 | Duffy . | |
| 5,057,710 | 10/1991 | Nishiura et al. | 307/400 |
| 5,062,158 | 11/1991 | Oka et al. | 2/46 |
| 5,077,468 | 12/1991 | Hamade . | |
| 5,090,975 | 2/1992 | Requejo et al. . | |
| 5,110,620 | 5/1992 | Tani et al. | 427/40 |
| 5,112,048 | 5/1992 | Deeds . | |
| 5,112,677 | 5/1992 | Tani et al. . | |
| 5,118,942 | 6/1992 | Hamade | 250/324 |
| 5,135,724 | 8/1992 | Dinter et al. . | |
| 5,138,971 | 8/1992 | Nakajima et al. . | |
| 5,143,767 | 9/1992 | Matsuura et al. . | |
| 5,149,335 | 9/1992 | Kellenberger et al. | 604/372 |
| 5,165,979 | 11/1992 | Watkins et al. | 428/113 |
| 5,169,706 | 12/1992 | Collier, IV et al. | 428/152 |
| 5,173,356 | 12/1992 | Eaton et al. | 428/219 |
| 5,178,932 | 1/1993 | Perkins et al. | 428/198 |
| 5,183,701 | 2/1993 | Jacobs et al. | 428/229 |
| 5,188,885 | 2/1993 | Timmons et al. | 428/198 |
| 5,204,174 | 4/1993 | Daponte et al. | 428/286 |
| 5,206,061 | 4/1993 | Ando et al. | 428/34.7 |
| 5,213,881 | 5/1993 | Timmons et al. | 428/224 |
| 5,213,882 | 5/1993 | Sassa et al. | 428/224 |
| 5,226,992 | 7/1993 | Morman | 156/62.4 |
| 5,230,727 | 7/1993 | Pound et al. | 55/492 |
| 5,232,770 | 8/1993 | Joseph | 428/284 |
| 5,238,733 | 8/1993 | Joseph et al. | 428/284 |
| 5,244,482 | 9/1993 | Hassenboehler, Jr. | 55/528 |
| 5,246,637 | 9/1993 | Matsuura et al. . | |
| 5,247,072 | 9/1993 | Ning et al. | 536/97 |

U.S. PATENT DOCUMENTS

| | | |
|---|---|---|
| 5,254,297 | 10/1993 | Deeds . |
| 5,256,176 | 10/1993 | Matsuura et al. .......................... 55/528 |
| 5,257,982 | 11/1993 | Cohen et al. ............................ 604/378 |
| 5,264,276 | 11/1993 | McGregor et al. ..................... 428/252 |
| 5,284,703 | 2/1994 | Everhart et al. ........................ 428/283 |
| 5,286,326 | 2/1994 | Greve ................................... 156/272.4 |
| 5,294,482 | 3/1994 | Gessner . |
| 5,306,534 | 4/1994 | Bosses .................................. 428/35.2 |
| 5,308,674 | 5/1994 | Zafiroglu ................................ 428/102 |
| 5,308,691 | 5/1994 | Lim et al. .............................. 428/286 |
| 5,336,545 | 8/1994 | Morman ................................ 428/152 |
| 5,350,620 | 9/1994 | Sundet et al. .......................... 428/172 |
| 5,389,202 | 2/1995 | Everhart et al. ........................ 162/103 |
| 5,397,413 | 3/1995 | Trimble et al. ........................ 156/167 |
| 5,401,446 | 3/1995 | Tsai et al. ............................... 264/22 |
| 5,407,581 | 4/1995 | Onodera et al. ....................... 210/654 |
| 5,409,766 | 4/1995 | Yuasa et al. ........................... 428/224 |
| 5,411,576 | 5/1995 | Jones et al. ............................... 95/57 |
| 5,436,033 | 7/1995 | Mino et al. . |
| 5,436,066 | 7/1995 | Chen ..................................... 428/288 |
| 5,441,550 | 8/1995 | Hassenboehler, Jr. .................... 55/486 |
| 5,443,606 | 8/1995 | Hassenboehler, Jr. .................... 55/486 |
| 5,455,108 | 10/1995 | Quincy et al. ......................... 428/266 |
| 5,456,972 | 10/1995 | Roth et al. ............................. 428/224 |
| 5,464,688 | 11/1995 | Timmons et al. . |
| 5,468,428 | 11/1995 | Hanschen et al. . |
| 5,472,481 | 12/1995 | Jones et al. ................................ 96/15 |
| 5,482,765 | 1/1996 | Bradley et al. . |
| 5,486,411 | 1/1996 | Hassenboehler, Jr. et al. ........ 428/286 |
| 5,491,022 | 2/1996 | Smith .................................... 428/224 |
| 5,493,117 | 2/1996 | Tamaki et al. ......................... 264/483 |
| 5,496,507 | 3/1996 | Angadjivand et al. ................. 264/423 |
| 5,503,745 | 4/1996 | Ogata et al. ........................... 210/490 |
| 5,540,979 | 7/1996 | Yahiaoui et al. ....................... 428/212 |
| 5,552,012 | 9/1996 | Morris et al. ........................ 156/272.4 |
| 5,637,165 | 6/1997 | Chen ..................................... 156/62.2 |
| 5,814,570 | 9/1998 | Cohen .................................... 442/346 |
| 5,834,384 | 11/1998 | Cohen et al. ........................... 442/382 |
| 5,834,386 | 11/1998 | Cohen .................................... 442/382 |

OTHER PUBLICATIONS

Patent Abstracts of Japan, vol. 11, No. 315 (C–451), Oct. 14, 1987 & JP,A,62 102809 (Mitsui Petrochem. Ind. Ltd.), May 13, 1987, see abstract & Database WPI, Section Ch, Week 8725, Derwent Publications Ltd., London, GB; Class A12, AN 87–172842 & JP,A,62 102 809 (Mitsui Petrochem. Ind. Co. Ltd.), May 13, 1987, see abstract.

Journal of Electrostatics, vol. 21, 1988, Amsterdam NL, pp. 81–98, XP002012022, P.A. Smith & G. C. East: "Generation of Triboelectric Charge in Textile Fibre Mistures, and their use as Air Filters", see document.

Database WPI, Section Ch, Week 8930, Derwent Publications, Ltd., London, GB; Class A94, AN 89–217687 XP002005648 & JP,A,01 156 578 (Showa Denko), Jun. 20, 1989, See Abstract.

An Introduction to Electrostatic Separation, Technical Bulletin, Bulletin 8570, Carpco, Inc. (No Date).

Electrostatic Separation of Mixed Granular Solids by oliver C. Ralston, Elsevier Publishing Company, 1961, Chapter IV, "Applications of Electrostatic Separation", pp. 134–234.

J. van Turnhout: Topics in Applied Physics, vol. 33, Chapter 3 "Thermally Stimulated Discharge of Electrets", pp. 81–215 (1980).

J. van Turnhout: Thermally Stimulated Discharge of Polymer Electrets, Chapter 1, pp. 1–24 (1975).

G.M. Sessler: Electronic Properties of Polymers, Chapter 3 "Charge Storage", pp. 59–107.

Patent Abstacts of Japan, vol. 007 No. 167 (C–177), Jul. 22, 1958 & JP,A,58 076118 (Kouken KK) May 9, 1983, See Abstract.

Patent Abstracts of Japan, vol. 011 No. 246 (C–439), Aug. 11, 1987 & JP,A,62 053719 (Japan Vilene Co. Ltd.) Mar. 9, 1987, See Abstract.

Patent Abstracts of Japan, vol. 011 No. 273 (C–445), Sep. 4, 1987 & JP,A,62 074423 (Japan Vilene Co. Ltd.) Apr. 6, 1987, See Abstract.

J. van Turnhout: Topics in Applied Physics, vol. 33, Chapter 3, pp. 81–225 (1980).

J. van Turnhout: Thermally Stimulated Discharge of Polymer Electrets, Chapter 1, pp. 1–24 (1975).

G.M. Sessler: Electronic Properties of Polymers, Chapter 3, pp. 59–107.

NONWOVEN BARRIER AND METHOD OF MAKING THE SAME

This application is a continuation of application Ser. No. 08/198,928 entitled "IMPROVED NONWOVEN BARRIER AND METHOD OF MAKING THE SAME" and filed in the U.S. Patent and Trademark Office on Feb. 22, 1994, now abandoned. The entirety of this Application is hereby incorporated by reference.

FIELD OF THE INVENTION

The present invention is directed to bacterial barrier fabrics. More particularly, the present invention is directed to nonwoven bacterial barrier fabrics for use as sterilization wrap, surgical draping, surgical gowns, cover garments, such as over-suits, and the like.

BACKGROUND OF THE INVENTION

As is generally known, surgical gowns, surgical drapes, surgical face masks and sterile wrap (hereinafter collectively "surgical articles") have been designed to greatly reduce, if not prevent, the transmission through the surgical article of liquids and/or airborne contaminants. In surgical procedure environments, such liquids sources include the gown wearer's perspiration, patient liquids, such as blood and life support liquids such as plasma and saline. Examples of airborne contaminants include, but are not limited to, biological contaminants, such as bacteria, viruses and fungal spores. Such contaminants may also include particulate material such as, but not limited to, lint, mineral fines, dust, skin squamae and respiratory droplets. A measure of a fabrics ability to prevent the passage of such airborne materials is sometimes expressed in terms of "filtration efficiency".

Many of these surgical articles were originally made of cotton or linen and were sterilized prior to their use in the operating room. Such surgical articles fashioned from these materials, however, permitted transmission or "strike-through" of various liquids encountered in surgical procedures. In these instances, a path was established for transmission of biological contaminants, either present in the liquid or subsequently contacting the liquid, through the surgical article. Additionally, in many instances surgical articles fashioned from cotton or linen provide insufficient barrier protection from the transmission therethrough of airborne contaminants. Furthermore, these articles were costly, and of course laundering and sterilization procedures were required before reuse.

Disposable surgical articles have largely replaced linen surgical articles. Advances in such disposable surgical articles include the formation of such articles from totally liquid repellent fabrics which prevent strike-through. In this way, biological contaminates carried by liquids are prevented from passing through such fabrics. However, in some instances, surgical articles formed from nonporous films, while being liquid and airborne contaminant impervious, are, or become over a period of time, uncomfortable to wear.

In some instances, surgical articles fashioned from liquid repellent fabrics, such as fabrics formed from nonwoven polymers, sufficiently repel liquids and are more breathable and thus more comfortable to the wearer than nonporous materials. However, these improvements in comfort and breathable provide by such nonwoven fabrics have generally occurred at the expense of barrier properties or filtration efficiency.

While the focus thus far has been directed to surgical articles, there are many other garment or over-garment applications, such as personal protective equipment applications, whose designers require both fabric comfort and filtration efficiency. Other personal protective equipment applications include, but are not limited to, laboratory applications, clean room applications, such as semiconductor manufacture, agriculture applications, mining applications, and environmental applications.

Therefore, there is a need for garment materials and methods for making the same which provide improved breathability and comfort as well as improved filtration efficiency. Such improved materials and methods are provided by the present invention and will become more apparent upon further review of the following specification and claims.

SUMMARY OF THE INVENTION

In response to the above problems encountered by those of skill in the art, the present invention provides a steam sterilizable nonwoven material, such as nonwoven fabrics, formed from polymer fibers. The nonwoven materials of the present invention are formed by subjecting a portion of the nonwoven material to charging, and more particularly to electrostatic charging, and then steam sterilizing the nonwoven material. The nonwoven material may be subjected to charging followed by steam sterilization or steam sterilization followed by charging. The nonwoven material may also be treated with an antistatic material before or after subjecting the nonwoven material to charging.

These methods further include positioning another nonwoven material in a juxtaposed relationship with the first nonwoven material. Portions of the other, or second, nonwoven material may be subjected to charging before or after steam sterilization. The second nonwoven material may also be treated with an antistatic material before or after being subjected to charging.

The nonwoven materials includes a steam sterilized web formed from fibers of a polymer wherein a portion of these fibers have been subjected to charging, and particularly electrostatic charging. The steam sterilized nonwoven composition may also include an antistatic material present about portions thereof. The above nonwoven composition may further include a second web in a juxtaposed relationship to the first web. The second web may be formed from polymer fibers wherein a portion of these fibers may be subjected to charging. An antistatic treatment may also be present about portions of the second web.

The composition of the present invention further includes a nonwoven material including a first web formed from fibers of a polymer, wherein a portion of these fibers have been subject to charging and wherein an antistatic material is present about portions of the first web. This composition may further include a second web formed from fibers of a polymer, wherein the polymer is positioned in a juxtaposed relationship with the first web. The second web may also be subjected to charging.

DETAILED DESCRIPTION OF THE INVENTION

Disclosed herein are compositions, and methods of making the same, which improved both the airborne contaminant barrier and filtration efficiency of a web formed from polymer fibers. Among the applications for such compositions and methods are included, but not limited to, applications requiring sterilizable, breathable materials having high airborne contaminant barrier properties. Such materials have application in surgical articles, such as gowns, drapes, sterile wrap and face mask, as well as other non-surgical applications such as agriculture, mining, clean room and environmental.

Polymers are well suited for the formation of nonwoven materials which are useful in the practice of the present invention. Nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of dielectric materials including, but not limited to, polyesters, polyolefins, nylon and copolymer of these materials. The fibers may be relatively short, staple length fibers, typically less than 3 inches, or longer more continuous fibers such as are produced by a spunbonding process.

It has been found that nonwovens formed from polyolefin-based fibers are particularly well-suited for the above applications. Examples of such nonwovens are the polypropylene nonwovens produced by the Assignee of record, Kimberly-Clark Corporation. And more particularly, the spunbond, meltblown, spunbond material produced by Kimberly-Clark Corporation.

This spunbond, meltblown, spunbond material may be made from three separate layers which are laminated to one another. Such a method of making this laminated material is described in commonly assigned U.S. Pat. No. 4,041,203 to Brock et al which is incorporated herein in its entirety by reference. Alteratively, the spunbond, meltblown, spunbond material may be made by first forming a spunbond, meltblown laminate. The spunbond, meltblown laminate is formed by applying a layer of meltblown on to a layer of spunbond. The second layer of spunbond is then applied to the meltblown side of the previously formed spunbond, meltblown laminate. Generally, the two outer layers provide the nonwoven fabric with strength while the inner layer provides barrier properties.

The nonwoven web of the present invention may be formed from a single layer or multiple layers. In the case of multiple layers, the layers are generally positions in a juxtaposed or surface-to-surface relationship and all or a portion of the layers may be bound to adjacent layers. The nonwoven web may also be formed from a plurality of separate nonwoven webs wherein the separate nonwoven webs may be formed from single or multiple layers. In those instances where the nonwoven web includes multiple layers, the entire thickness of the nonwoven web may be subjected to charging or individual layers may be separately subjected to charging and then combined with other layers in a juxtaposed relationship to form the finished nonwoven web.

Methods of subjecting a material to charging, and particularly electrostatic charging, are well known by those skilled in the art. These methods include, for example, thermal, liquid-contact, electron beam and corona discharge methods. One particular technique of subjecting a material to electrostatic charging is the technique disclosed in U.S. Pat. No. 5,401,446 Feb. 29, 1996 herein incorporated in its entirety by reference. This technique involves subjecting a material to a pair of electrical fields wherein the electrical fields have opposite polarities.

Sterilization of the nonwoven web may be accomplished by several techniques which include chemical and steam techniques. In those instances when the nonwoven web is used to wrap surgical instruments, steam sterilization techniques are commonly used. In such instances, the unsterile instruments are first wrapped in the nonwoven web. The wrapped instruments are then steam sterilized. The instruments, still wrapped, are then removed from the steam sterilizing equipment or autoclave and are stored in the wrapping material until needed. When needed, the wrapping web is removed making the instruments available for handling.

The steam sterilization cycle may vary dependent upon type of sterilizer and the size/quantity of the items being sterilized. For example, the time and temperature parameters for gravity-displacement cycles may range from 10 to 15 minute exposure time at 270° F. to 275° F. to 15 to 30 minute exposure time at 250° F. to 254° F. For pre-vacuum cycles, the time and temperature parameters may be 3 to 4 minutes at 270° F. to 275° F. And for steam-flush pressure-pulse cycles, the time and temperature parameters may range from 3 to 4 minutes at 270° F. to 275° F. to 20 minutes at 250° F. to 254° F.

In those instances where the nonwoven web is used in or around flammable materials and static discharge is a concern, the nonwoven web may be treated with any number of antistatic materials. In these instances, the antistatic material may be applied to the nonwoven by any number of techniques including, but not limited to dipping the nonwoven into a solution containing the antistatic material or by spraying the nonwoven with a solution containing the antistatic material. In some instances the antistatic material may be applied to both the external surfaces of the nonwoven and the bulk of the nonwoven. In other instances, the antistatic material may be applied to portions of the nonwoven, such as a selected surface or surfaces thereof.

Of particular usefulness is the antistatic material known as ZELEC®, an alcohol phosphate salt product of the Du Pont Corporation. The nonwoven web may be treated with the antistatic material either before or after subjecting the web to charging. Furthermore, some or all of the material layers may be treated with the antistatic material. In those instances where only some of the material layers are treated with antistatic material, the non-treated layer or layers may be subjected to charging prior to or after combining with the antistatic treated layer or layers.

To demonstrate the attributes of the present invention, the following Examples are provided.

EXAMPLE 1

Kimberly-Clark manufactures a series of single sheet laminate nonwoven web materials made from spunbond-meltblown-spunbond (SMS) layers. These materials are available in a variety of basis weights. The nonwoven web materials used in Examples 1 and 2 were such single sheet laminate materials sold by Kimberly-Clark under the mark KIMGUARD® Heavy Duty Sterile Wrap. The basis weight of this material is 2.2 oz/sq yd. Both spunbond layers have a basis weight of 0.85 oz/sq yd and the meltblown layer has a basis weight of 0.50 oz/sq yd.

The method used to subject the samples reported in Tables 1–4 to electrostatic charging is described in the above referenced U.S. Pat. No. 5,401,446.

Referring now to Table 1, a summary of bacterial filtration efficiency (BFE) test results and standard deviation (SD) are reported for three categories investigated for Heavy Duty KIMGUARD® Sterile Wrap. The first category, "Uncharged" reports the average BFE for eleven samples of ZELEC® treated and eleven samples of non-ZELEC® treated KIMGUARD® material. These samples were not subjected to electrostatic charging or steam sterilization.

The second category, "Charged", reports the average BFE for eleven samples of ZELEC® treated and eleven samples of non-ZELEC® treated KIMGUARD® material which were subject to electrostatic charging but not steam sterilization.

The third category, "Charged/Sterilized" reports the average BFE for eleven samples of ZELEC® treated and eleven samples of non-ZELEC® treated KIMGUARD® material which were first charged then steam sterilized. Sterilization of these samples was accomplished in an Amsco 2021 Gravity Sterilizer, a product of American Sterilizer Co. of Erie, Pa. Samples were sealed in a Baxter DUAL PEEL™ Self Seal Pouch. The sealed pouches were exposed to 250° F. at 15 psi steam for 20 minutes with a dry time of 5 minutes. After sterilizing, the above samples were analyzed by Nelson Laboratories for Bacterial Filtration Efficiency testing.

TABLE 1

Bacterial Filtration Efficiency
(KIMGUARD ® Heavy Duty Sterile Wrap)

| Description | Uncharged | Charged | Charged/Sterilized |
|---|---|---|---|
| ZELEC ® | 85.55+/−2.38 | 93.85+/−3.67 | 95.87+/−0.99 |
| Non-ZELEC ® | 82.18+/−1.66 | 96.36+/−1.72 | 93.64+/−2.72 |

As previously stated, Nelson Laboratories of Salt Lake City, Utah preformed the above BFE analysis. The procedure used to determine these BFEs is described in Nelson Laboratories' Protocol No. ARO/007B in accordance with MIL Spec 36954C, 4.4.1.1.1 and 4.4.1.2.

Example 2

Further analysis of the Heavy Duty KIMGUARD® Sterile Wrap (2.2 oz) were conducted to determine BFE and the charge on the samples for both pre- and post-steam sterilizing. Steam sterilization of the samples reported in Example 2 was accomplished using the steam sterilization procedure reported in Example 1. The BFE results reported in Table 2 were the product of Nelson Laboratories using the protocol described in Example 1. These BFE results represent the average of eleven non-antistatic treated samples.

TABLE 2

Bacterial Filtration Efficiency
(KIMGUARD ® Heavy Duty Sterile Wrap)

| Description | BFE | SD % | Charge Pre | Charge Post |
|---|---|---|---|---|
| Uncharged | 90.6 | 2.3 | — | — |
| Charged | 98.8 | 0.31 | 800–1000 v/cm2 | — |
| Charged/ Sterilized | 94.4 | 2.0 | — | 100–180 v/cm2 |

After charging but before steam sterilizing, a voltage of between 800 to 1,000 volts/cm$^2$, positive on one side of the material and negative on the other side of the material, was recorded. After steam sterilizing, a voltage of between 100 to 180 volts/sq cm, positive on one side and negative on the other side, was recorded. In both instances, voltage was measured using an Electrostatic Voltmeter (Trek Model 344, Trek, Inc, Median, N.Y.) by taking ten readings on each side of the samples.

Example 3

Further barrier properties for SMS fabric samples were investigated. Table 3 reports the barrier property results for KIMGUARD® Heavy-Duty Sterile Wrap (KIM) and SPUNGUARD® Regular Sterilization Wrap (SPU). SPUNGUARD® Regular Sterilization Wrap is also a spunbond, meltblown, spunbond material having a basis weight of 1.05 oz/sq yd (0.35/0.35/0.35). These categories included ZELEC® treated and non-ZELEC® treated materials, charged and non-charged, sterilized and non-sterilized material.

The charged and sterilized samples were prepared according to the charging and sterilizing procedures described in Example 1 except that all sterilized sample pouches were conditioned at laboratory ambient environment for at least 4 hours prior to testing. For samples 1 and 2, the barrier properties were measured using the Nelson procedures described in Example 1. For samples 3–13, the barrier properties were measured using a microbial challenge procedure described below.

In runs 3–13, a six port exposure chamber was used. Five of the ports accommodated five separate samples. The challenge control filter material was positioned in the sixth port. Three conditions were maintained in the microbial challenge test. These were: first, a 2.8 LPM (Liters Per Minute) flowrate through each of the ports; second, an exposure time of fifteen minutes followed by a chamber exhaust of fifteen minutes, and; third, a microbial challenge that results in 1×10 E6 CFU's (Colony Forming Units) per port. Bacillus subtilis ss globigii spores, purchased from Amsco (Part No. NA-026, P-764271-022) was used to make the working spore suspension of 1×10 E6 CFUs per port recovery.

TABLE 3

| Sample | Product | ZELEC ® | Charged | Sterilized | Avg % Red | SD | n |
|---|---|---|---|---|---|---|---|
| 1 | SPU | No | No | Yes | 71.5 | 9.1 | 25 |
| 2 | SPU | No | Yes | Yes | 87.2 | 3.1 | 25 |
| 3 | KIM | Yes | No | Yes | 69.4 | 5.7 | 15 |
| 4 | KIM | Yes | Yes | Yes | 80.8 | 9.1 | 15 |
| 5 | KIM | Yes | Yes | No | 97.2 | 1.1 | 15 |
| 6 | KIM | Yes | No | Yes | 80.1 | 9.2 | 15 |
| 7 | KIM | Yes | Yes | Yes | 88.9 | 5.7 | 15 |
| 8 | KIM | Yes | Yes | No | 94.6 | 2.7 | 15 |
| 9 | KIM | Yes | No | Yes | 73.9 | 7.6 | 15 |
| 10 | KIM | Yes | Yes | Yes | 86.2 | 4.1 | 15 |
| 11 | KIM | No | No | Yes | 66.8 | 11.9 | 15 |
| 12 | KIM | No | Yes | Yes | 94.5 | 2.8 | 15 |
| 13 | KIM | NO | Yes | No | 98.2 | 0.7 | 15 | n - Number of fabric samples.

The average percent reduction (Avg % Red) is a measurement of filtration efficiency. The Avg % Red is an expression of the reduction of number of colony forming units (CFUs) or bacteria passing through a sample compared to the number CFUs in the challenge control filter material. The Avg % Red was calculated by subtracting the number of CFUs passing through a sample from the number of CFUs passing through the challenge control filter material and dividing this number by the number of CFUs for the challenge filter material. The result was then multiplied by 100 to convert to percent.

Table 3 demonstrates that filtration properties of the steam sterilized nonwoven samples are improved by the charging of the fabric samples (Samples 2, 4, 7, 10, and 12) as compared to samples which have not been subjected to charging (Samples 1, 3, 6, 9, and 11).

Example 4

Table 4 reports charge data for the top and bottom surfaces of 2.2 oz. KIMGUARD® fabric samples subjected to various conditions. As noted in Table 4, one of the KIMGUARD® samples was treated with ZELEC® and the other was not. Except as otherwise indicated, the measurements were made on separate samples. Each sample was had a general dimension of about 10"×10". The area of each sample measured had a general dimension of about 6"×6". Measurements were taken each ½" in a 12×12 matrix. The charge number reported is an averaged number. The equipment used to measure charge was the same as described in Example 2.

TABLE 4

AVERAGE SURFACE VOLTAGE OF SAMPLES OF 2.2 OZ KIMGUARD ® STERILE WRAP

| Sample # Material | Side | 1 As Received | 2 Charge | 3 Sterilizer 20 min. in Dual Peel Pouch | 4 Sterilizer 60 min. in Dual Peel Pouch | 5 Sample #3 No Pouch Sterilizer 20 min. | 6 Sample #4 No Pouch Sterilizer 60 min. |
|---|---|---|---|---|---|---|---|
| Kimguard | A | −2.8 | −125 | −51 | −100 | 30 | −43 |
| (ZELEC ®) | B | 1.6 | −15 | −48 | −169 | 72 | 66 |
| Kimguard | A | −61 | 272 | 239 | −353 | −146 | −354 |
| (Non-ZELEC ®) | B | −87 | −432 | −265 | −243 | −232 | −223 |

Notes:
Sample #5 rerun of #3 without pouch
Sample #6 rerun of #4 without pouch

As demonstrated by the above Examples, the barrier properties of steam sterilized non-woven material are improved when these materials are subjected to charging, and particularly electrostatic charging. It will be further observed that the barrier properties of an antistatic treated non-woven material are improved when these materials are subjected to charging, and particularly electrostatic charging.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. A method of manufacturing nonwoven material comprising:

charging a nonwoven web;

treating the nonwoven web with an antistatic material; and wherein the nonwoven web is treated with the antistatic material prior to being charged.

2. The method of claim 1 wherein the charging is electrostatic charging.

3. A nonwoven material made by the method of claim 2.

4. The method of claim 1 wherein the nonwoven material comprises first and second nonwoven webs joined together in juxtaposed relationship.

5. A nonwoven material made by the method of claim 4.

6. The method of claim 4 wherein the webs are joined after the charging step.

7. The method of claim 6 wherein the first web is charged and the second web is not charged.

8. A nonwoven material made by the method of claim 6.

9. A nonwoven material made by the method of claim 7.

10. A nonwoven material made by the method of claim 1.

11. The method of claim 1 wherein the nonwoven web is dipped into a solution containing the antistatic material.

12. The method of claim 1 wherein a solution containing the antistatic material is sprayed onto the nonwoven web.

13. The method of claim 1 wherein the antistatic material is further defined as an alcohol phosphate salt.

14. A method of manufacturing nonwoven material wherein the nonwoven material includes a plurality of nonwoven webs comprising:

charging at least one of the webs;

treating at least one of the webs with an antistatic material; and wherein the treating step precedes the charging step.

15. A nonwoven material made by the method of claim 14.

16. The method of claim 14 wherein a portion of at least one of the webs is charged.

17. The method of claim 14 wherein a portion of at least one of the webs is treated with an antistatic material.

18. A method of manufacturing nonwoven material comprising:

electrostaticly charging a nonwoven web;

treating the nonwoven web with an alcohol phosphate salt antistatic material;

wherein the nonwoven material is treated with the antistatic material prior to being electrostaticly charged.

19. The method of claim 18 wherein the nonwoven material comprises first and second nonwoven webs joined together in juxtaposed relationship.

20. The method of claim 19 wherein the webs are joined after the charging step.

21. A nonwoven material made by the method of claim 18.

* * * * *